United States Patent [19]

Lane et al.

[11] Patent Number: 4,928,065
[45] Date of Patent: May 22, 1990

[54] VOLTAMMETRY IN LOW-PERMITIVITY SUSPENSIONS

[75] Inventors: Gregg A. Lane, Kennett Square, Pa.; Kathryn Pearlstine, Wilmington, Del.

[73] Assignee: E. I. Du Pont de Nemours and Company, Wilmington, Del.

[21] Appl. No.: 331,990

[22] Filed: Mar. 31, 1989

[51] Int. Cl.$^5$ .................. G01N 27/42; G01N 27/04
[52] U.S. Cl. .................. 324/464; 324/439; 324/453; 204/153.1
[58] Field of Search .......... 204/1 T; 324/61 P, 61 R, 324/65 P, 65 R, 71.1, 453, 464, 439, 442, 444, 446, 448, 449

[56] References Cited

U.S. PATENT DOCUMENTS

| | | | |
|---|---|---|---|
| 3,844,940 | 10/1974 | Kopf et al. . | |
| 3,906,353 | 9/1975 | Murdock | 324/442 |
| 3,906,354 | 9/1975 | Murdock | 324/448 |
| 4,119,909 | 10/1978 | DeBerry | 324/439 |
| 4,132,944 | 1/1972 | Bentz | 324/442 |
| 4,227,151 | 10/1980 | Ellis | 324/448 |
| 4,336,111 | 6/1982 | Graunke . | |
| 4,411,741 | 10/1983 | Janata . | |
| 4,443,763 | 4/1984 | Marsoner | 324/439 |
| 4,528,270 | 7/1985 | Matsunaga . | |
| 4,631,116 | 12/1986 | Ludwig . | |
| 4,654,126 | 3/1987 | Amelio et al. . | |
| 4,725,339 | 2/1988 | Bindra et al. . | |
| 4,735,691 | 4/1988 | Green et al. . | |

FOREIGN PATENT DOCUMENTS

| | | | |
|---|---|---|---|
| 8700284 | 1/1987 | European Pat. Off. | 324/439 |
| 1607956 | 9/1970 | Fed. Rep. of Germany | 324/439 |
| 0001545 | 1/1985 | Japan | 324/439 |

OTHER PUBLICATIONS

Wells; "The Question of Instrumental Artifact in Linear Sweep Voltammetry . . . " Analitye Chemistry–Jan. 1971–USll 324/439.

Primary Examiner—Rienhard J. Eisenzopf
Assistant Examiner—Jose M. Solis

[57] ABSTRACT

A method and apparatus for classifying non-aqueous liquid suspensions of charged particles employs a large time-varying electric field applied to a suspension situated between capacitive test electrodes. A current waveform is produced that characterizes the suspension with respect to critical properties including concentration, mobility, and plating tendencies of the charged particles suspended therein. The approach is suitable for use with suspensions having relative permitivity constants of about 15 or less.

21 Claims, 12 Drawing Sheets

Fig. 1
(Related Art)

KII 35 mg/g bbp 1.95 % solids

Q(inc.dc) = 1.258uC    Q(exc.dc) = .769uC    CONDUCT. = 44.38puho/cm
                                                              1.00 kv

VOLTAMMETRY IN LOW-PERMITIVITY SUSPENSIONS

BACKGROUND OF THE INVENTION

1. Field of the Invention

This invention relates to capacitive voltammetry, and more specifically to capacitive voltametric measurements involving the application of relatively large time-varying electric fields to low-permitivity non-aqueous liquid suspensions of charged particles.

2. Description of the Prior Art

Non-aqueous suspensions of charged particles are employed in many diverse art areas, such as paints, cosmetics, ceramics, and electrostatic toners for copying machines.

Examples of such suspensions include:

(1) Oxides, carbides, and nitrides of such materials as aluminum, beryllium, titanium, zirconium, silicon and boron suspended in non-aqueous media for use in fabrication of electronic materials. These materials include substrates, IC packages, insulators, capacitors, thermistors, varisitors, and other materials for the electronics industry;

(2) Liquid electrostatic toners which consist of pigment dispersions in non-aqueous liquid;

(3) Suspensions of iron oxides to produce magnetic recording disks; and (4) Dispersions of pesticides.

These are distinct from other chemical compositions in that:

(a) these materials consist of a dispersion of particles suspended in a liquid; and (b) the particles are charged, usually by addition of a surfactant, either to control deposition or to enhance stability of the dispersion.

Figure 1:
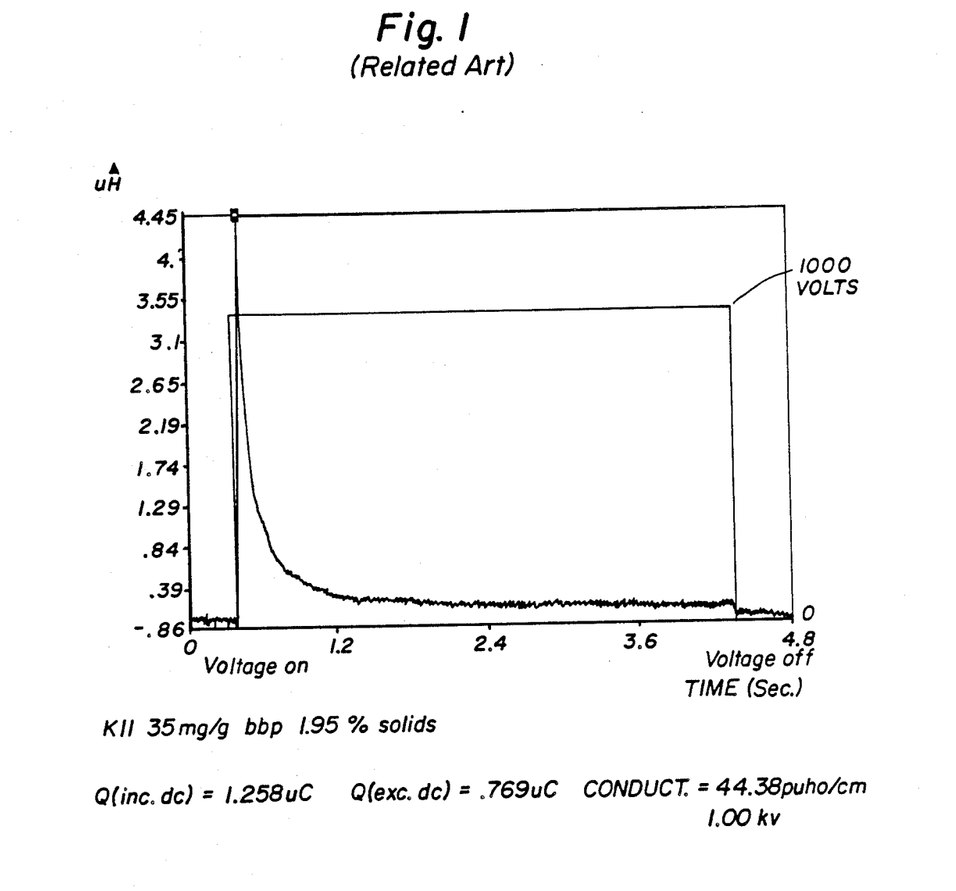
FIG. 1 shows the step-function test voltage waveform and the resultant time domain transient test current waveform of the prior art.

An elementary form of voltammetry has been employed and marketed by the Indigo Company, Rehovot, Israel in an effort to characterize properties of electrostatic toner suspensions. That company's CHARGEMETER with PCI Data Acquisition System instrument applies a step voltage to two capacitive electrodes having a sample of toner displaced therebetween. The resulting transient current versus time waveform is recorded, and correlations are made with standardized data in order to draw certain conclusions about characteristics of the toner. Typical test waveforms thereof are shown in FIG. 1. Based on the height, width, and time displacement transient waveform, an operator can obtain useful approximate values for charge to mass ratio of the sample and conductivity of the sample at the applied voltage. That approach is somewhat useful, but it is limited in that the contributions to the current from the particles and the surrounding solution cannot easily be separated and the response of the materials as a function of frequency of the applied voltage cannot be determined.

It is therefore an object of the instant invention to provide an improved measurement technique that will result in more complete and accurate characterizations of nonaqueous liquid suspensions of charged particles.

It is another object of this invention to use the test results obtained to accomplish monitoring and automatic control of machinery and processes that employ non-aqueous liquid suspensions of charged particles.

These and other objects of the invention will become more clear to the reader upon careful perusal of the following Summary, Drawing, Detailed Description and appended Claims.

SUMMARY OF THE INVENTION

The invention is directed to novel methodology and apparatus for characterization of pertinent properties of low-permitivity non-aqueous liquid suspensions of charged particles, and for monitoring and controlling processes and equipment employing such suspensions.

By sequentially applying large-magnitude time-varying electric fields of various time-waveform shapes and frequencies to suspensions of the subject genre, Applicants have discovered that the resulting electric current versus time waveforms contain valuable information which can be used to distinctly characterize important properties of the suspensions, including concentration, mobility, and adherence capability of the suspended charged particles. Knowledge thus gleaned can be used by those skilled in the art areas involving such suspensions to develop improved suspension compositions for specific applications. Furthermore, such knowledge can be quantified and catalogued in such a manner so as to allow for automatic monitoring and control of specific suspension properties.

Figure 2:
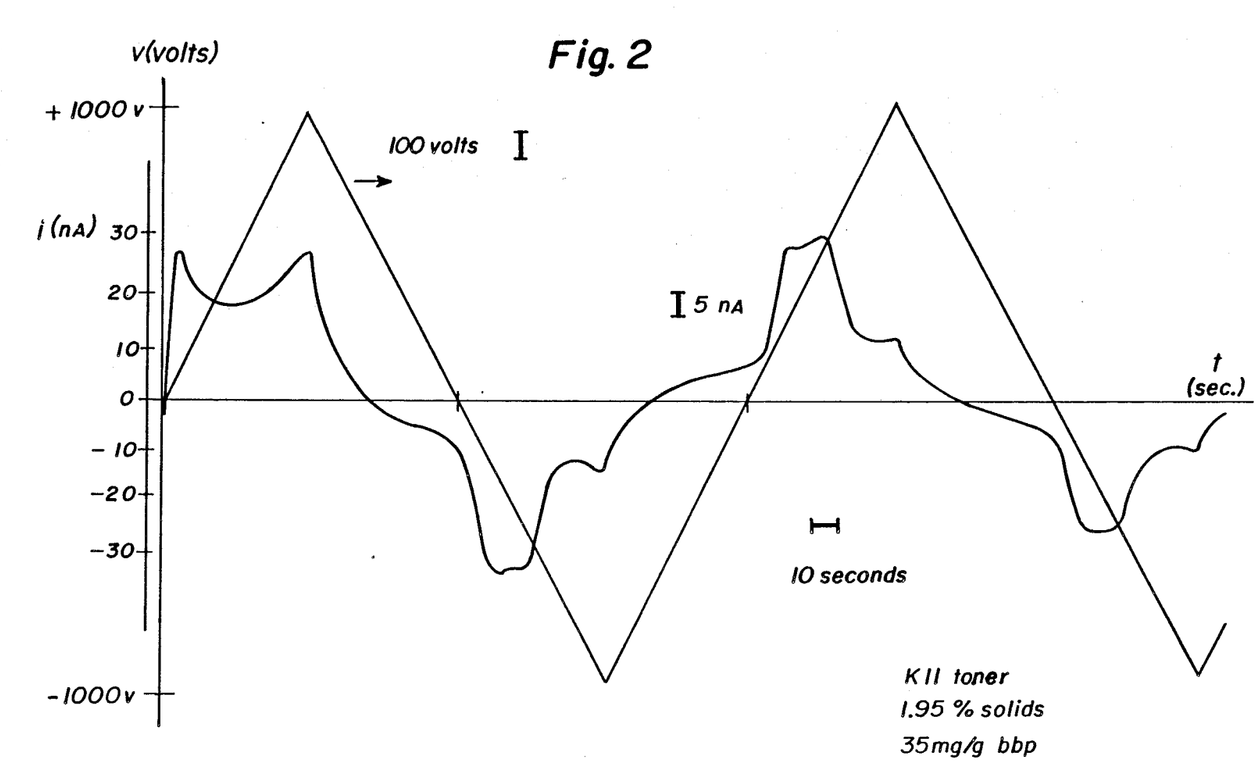
FIG. 2 depicts a typical low-frequency test voltage and resultant current waveform versus time according to the instant invention.

One embodiment of the invention comprises the application of a slowly-varying alternating linear ramp high peak voltage waveform, such as is depicted in FIG. 2, across a suspension of the above-described type via the electrodes of a parallel-plate capacitor cell, the plates of which are approximately 3 cm in diameter and spaced approximately 0.5 mm apart. The shape of the resultant current waveform is then correlated to previously collected empirical data so as to determine various characteristics of the test sample.

Figure 3A:
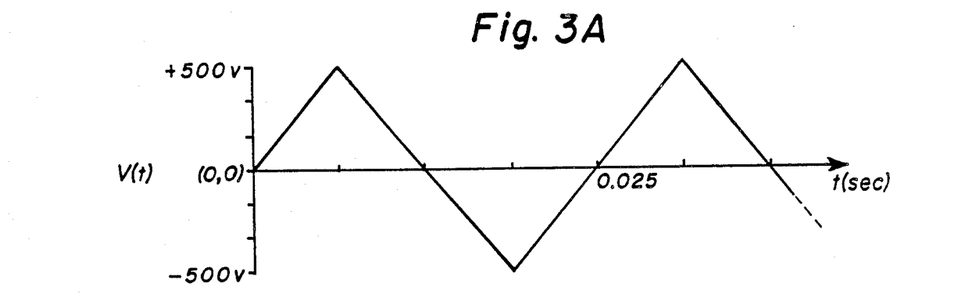
FIG. 3A shows a typical higher-frequency test voltage.
Figure 3B:
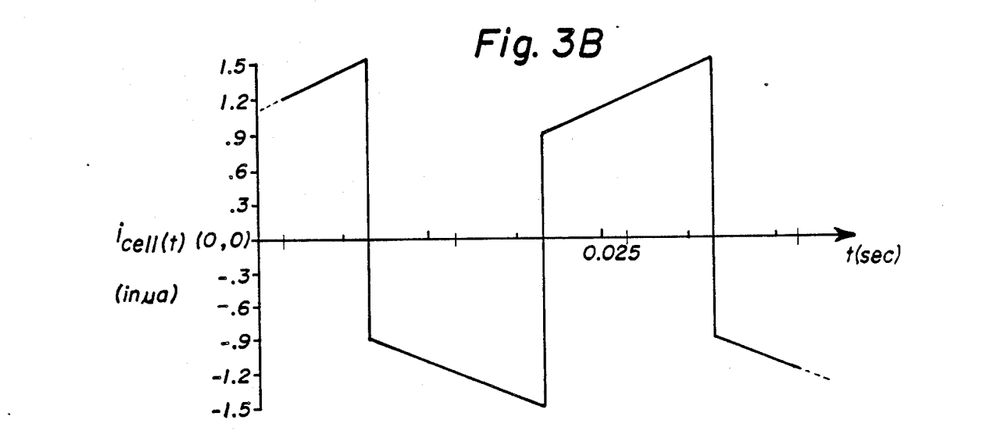
FIG. 3B shows a typical resultant current waveform when the test suspension includes charged particles.
Figure 3C:
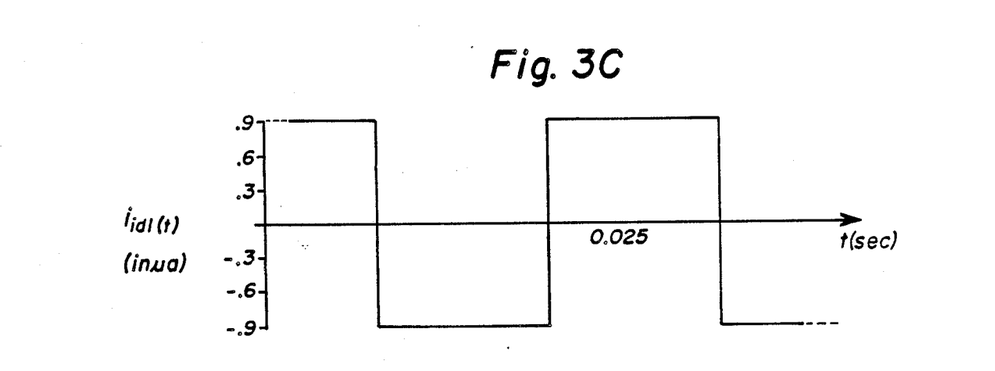
FIG. 3C shows the resultant current waveform for a suspension without charged particles.

In another embodiment of the invention an applied voltage waveform (as depicted in FIG. 3A) of substantially the same shape as described above, but of much higher frequency of repetition, is used to test the sample suspension. Due to the higher frequency of repetition of the applied waveform, the charged particles in the suspension do not have time to plate out at all on either of the capacitor's plates. As a result, the resultant steady-state cell current waveform (as depicted in FIG. 3B) magnitude is simply related to the concentration of the suspended charged particles and their mobility. FIG. 3C shows the current waveform without charged particles in the suspension. With this embodiment the relative magnitudes of previously collected empirical data are correlated with those of the test data to determine the concentration or mobility of the charged particles in the test sample.

In yet another embodiment of the invention, test results obtained as described above are used to modulate an automatic control system so as to maintain a crucial suspension property (such as charged particle concentration) within a desired range.

For all aspects of the invention the relative dielectric constant of the suspension must be in the neighborhood of 15 or less. The reason for this restriction is that the conductivity of high dielectric materials is too great to get measurements of particle charge; the voltage would be dropped at the liquid interface and may cause chemical decomposition of the suspending liquid.

For low-frequency applied waveforms the test capacitor cell of the invention becomes a non-linear device, whereas for the higher-frequency applied waveforms the capacitor performs in a substantially linear manner. This dual nature of the system allows for the efficient determination of heretofore relatively difficult t obtain suspension characteristics. Also, the use of a capacitive cell permits distinctions to be made between resulting test current components based on whether they vary significantly as a function of time rate of change potential gradient -capacitive components do, but resistive components do not. Hence the method and apparatus of the instant invention is novel and very useful for test equipment and control systems in many related art areas involving non-aqueous suspensions.

DETAILED DESCRIPTION

Figure 5:
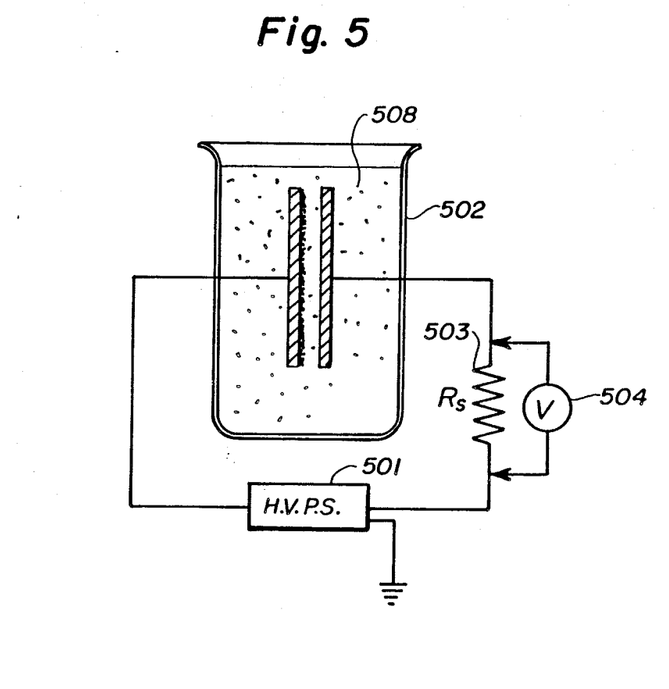
FIG. 5 is a schematic diagram of a test circuit comprising an implementation of the instant invention.

FIG. 5 shows a schematic diagram of a measurement system illustrative of the invention in which the output (such as shown in FIGS. 2 or 3) of a high voltage time-varying voltage source 501 is used to energize a series circuit comprising capacitive test cell 502 (including test suspension 508) and current sensing resistor 503. High-impedance voltmeter 504 is employed to monitor the voltage across resistor 503, which voltage, by Ohm's law, corresponds directly to the current in the series circuit. The distance d between the capacitive plates is preferably in the range between 0.25 mm and 1.0 mm.

Figure 4:
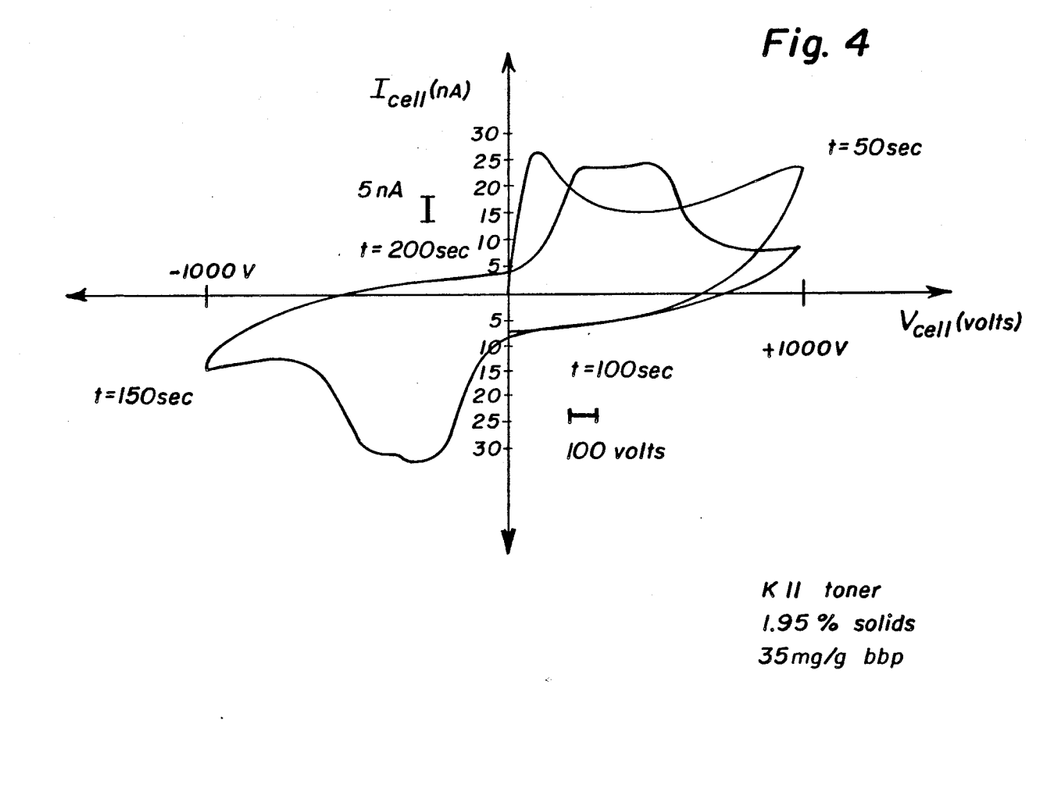
FIG. 4 shows a graph according to the instant invention wherein the resultant test current is plotted versus the applied voltage for a low-frequency test sample.

For laboratory purposes, voltmeter 504 may comprise a standard volt meter or a chart recorder to give an indication of the series circuit current as a function of time, or an "x-y" recorder to give the series circuit current as a function of the applied voltage v(t). The graphical approach as depicted in FIG. 4 is especially amenable to laboratory implementation and human interpretation. Not unlike the cardiologist's technique in reading electrocardiagrams, the technique of the instant invention (as applied to the type of graph shown in FIG. 4) currently involves human scrutiny of the graph to detect various characteristics of the suspension being tested. Insofar as computer analysis is developed and perfected for such purposes, the need for the human element may eventually be diminished or eliminated. In either case, the suspension "fingerprint" is compared with those of known characteristics in order to draw conclusions about the nature of the suspension being tested.

In an automatic control system, to control charged particle concentration for example, the voltage across Rs is used as a control voltage that indicates to the system when additional charged particles need to be added to the suspension in order to maintain a minimum desired concentration. This approach would employ a higher frequency applied high voltage waveform such as depicted in FIG. 3A.

Figure 8:
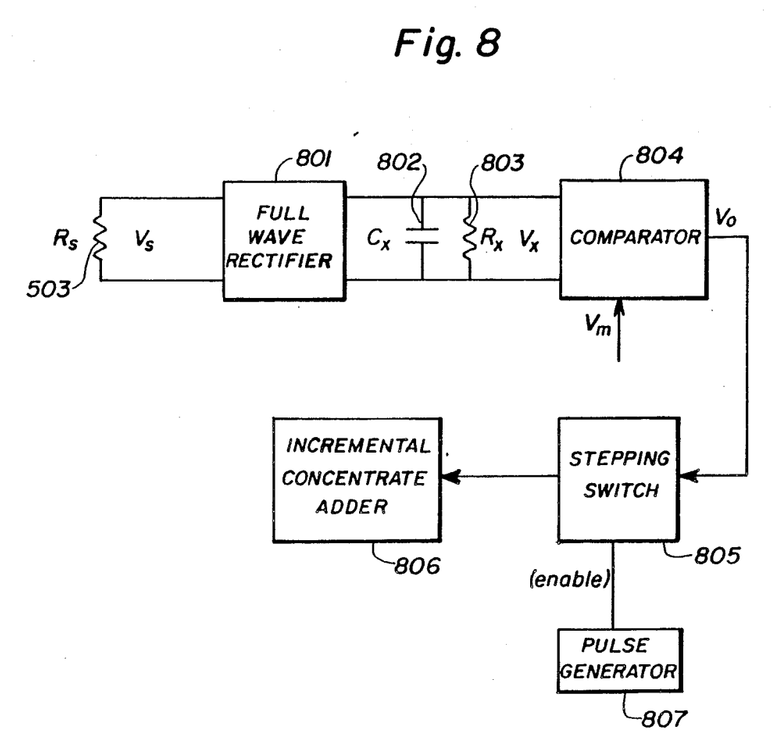
FIG. 8 depicts a block diagram of an automatic control system employing the instant invention.
Figure 9:
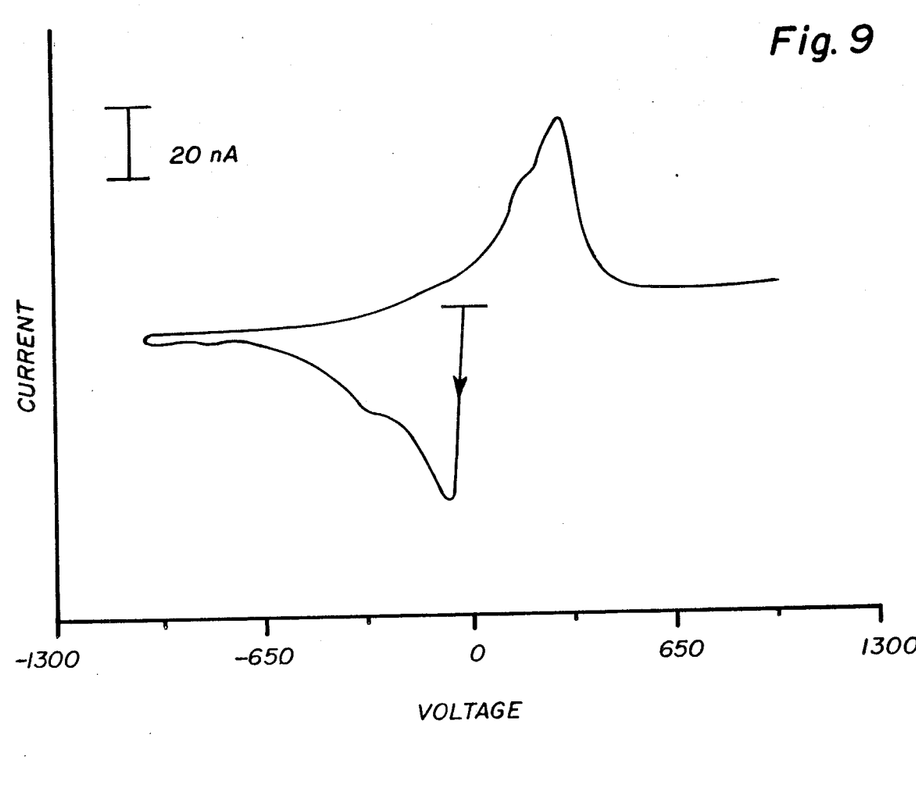
FIG. 9 shows the current response due to toner sweepout and transfer from an indium tin oxide (ITO) electrode. Magenta toner particles suspended in Isopar L (1.5%) solids are electrically attracted to the ITO electrode, and when the voltage is reversed the particles are removed from the electrode. Motion of the charged particles gives rise to the capacitive current shown in the figure. The voltage at which the current peak occurs gives a measure of the adhesion of the toner particles to the surface. The measurements were made in a cell 0.5 mm wide and 10 cm² area.
Figure 10:
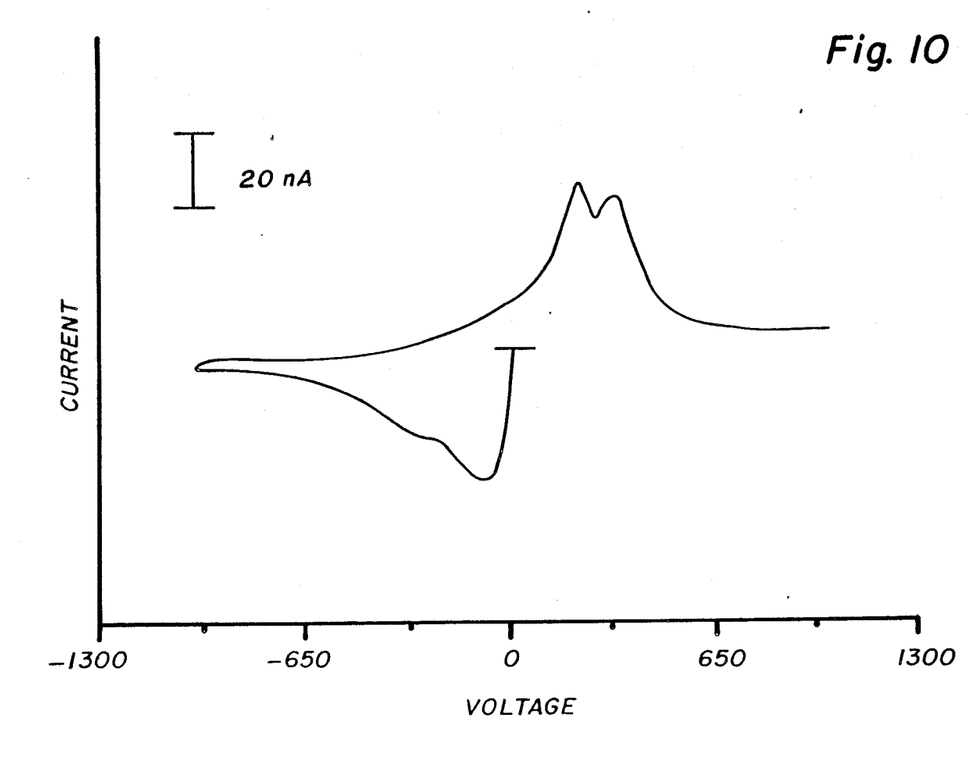
FIG. 10 shows results comparable to those as described for FIG. 9 except that here the ITO electrode is coated with Elvacite ® which has weaker adhesion to the toner layer than ITO.
Figure 11:
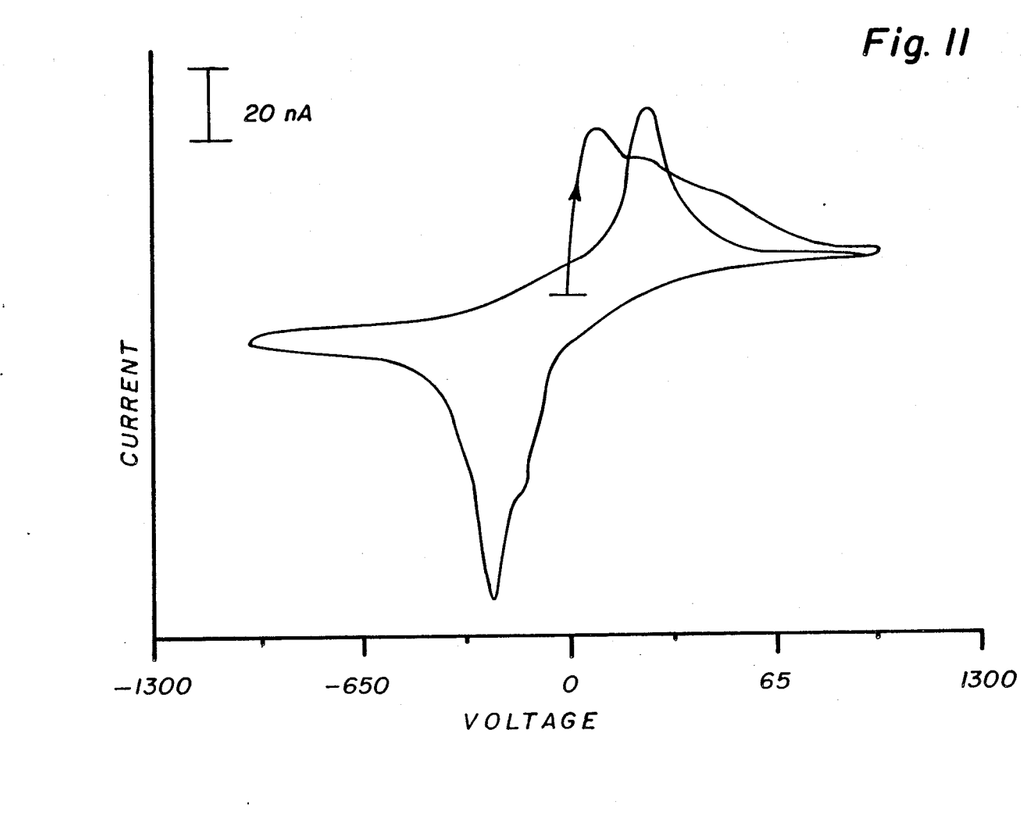
FIG. 11 displays results for cyan toner (1.5% solids) cyclic voltammetry in cell 1 mm gap and 10 cm² area. The electrodes are aluminum and indium tin oxide. Toner is initially attracted to the aluminum electrode.
Figure 12:
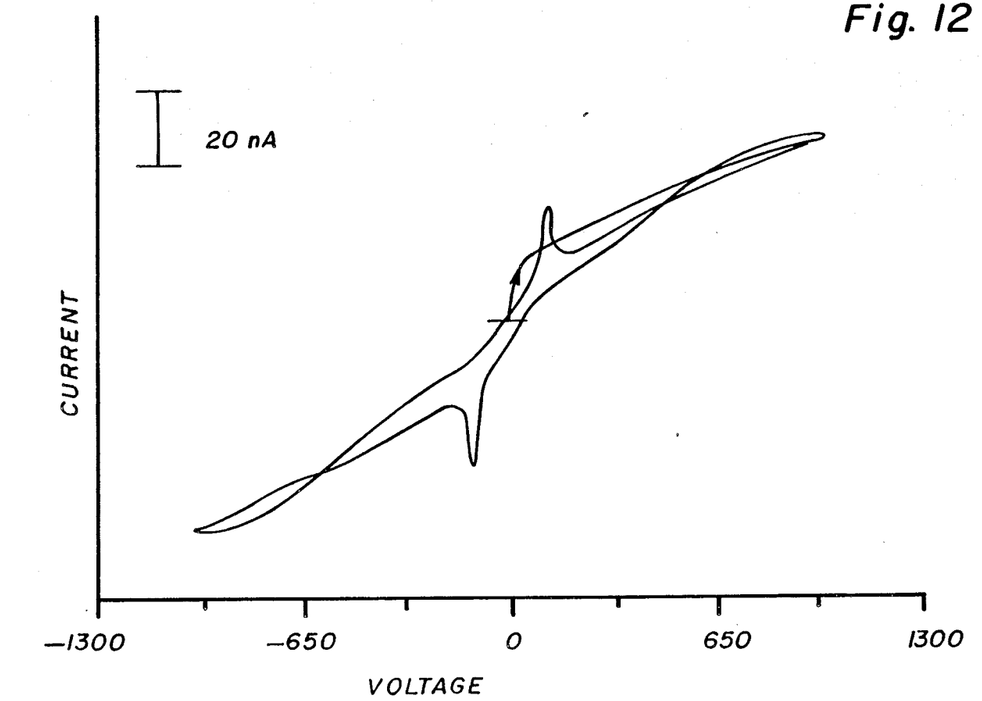
FIG. 12 shows reasults according to the system described for FIG. 11 except that here Triton X-35 (Rohm and Haas) has been added to the toner suspension.

FIG. 8 shows a block diagram of such a control system. The voltage $V_s$ across series resistor 503 is rectified by full wave rectifier 801 and averaged by charging capacitor 802 and bleed resistor 803. The resultant voltage $V_x$ is used as an input to comparator 804. When $V_x$ becomes lower than a preset value $V_m$, the comparator output $V_o$ goes high (e.g. +5 volts), thus energizing stepping switch 805 which in turn activates incremental concentrate adder 806. When additional charged particles are thus added to the suspension, $V_x$ increases above $V_m$, and the comparator output $V_o$ returns to zero. The stepping switch 805 is thus deactivated and incremental concentrate adder 806 is stopped. In a preferred embodiment stepping switch 805 is enabled only intermittently at regular intervals by pulse generator 809 so that when an incremental amount of concentrate is added to the suspension there will be adequate time for the system to determine if that amount is enough to get the charged particle concentration back up above the desired value. This arrangement acts to avoid unnecessary "overshoot" in the concentration level.

In another automatic system, higher frequency sinusoidal current levels are monitored and used as a control factor t modify the mobility of the suspended charged particles in a manner analogous to that described above. Generally, higher sinusoidal current corresponds to a higher charged-particle mobility in the suspension, all other factors being substantially constant. Hence surfactant might be added to the suspension automatically as needed for the purpose of controlling the overall mobility factor of the suspension.

Figure 6:
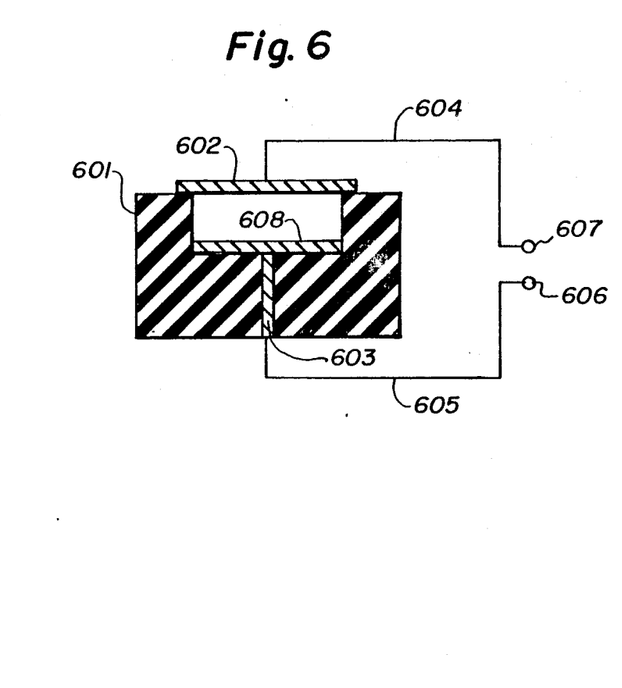
FIG. 6 is a cross-sectional pictorial view of a capacitive test cell in accordance with the instant invention.

FIG. 6 shows a cross-section of a capacitive test cell useful in connection with the instant invention. The base 601 is a solid electrically insulating substantially cylindrical mass with a cylindrically-shaped cavity contained therein. At the bottom of the cavity is an electrically-conducting bottom plate 608 connected to an electrically conducting column 603 that extends through base 601 as shown. Wire 605 joins column 603 with connecting terminal 606. Electrically conducting top plate 602 rests on the top surface of base 601 and completely covers the cavity in base 601. Wire 604 joins top plate 602 with connecting terminal 607. When the cavity between plates 602 and 608 is filled with a fluid suspension, the entire cell acts as a capacitor with value $C_t = K_d \epsilon_0 A/y$ (wherein $K_d$ is the relative permitivity constant fluid suspension contained therein, $\epsilon_0$ is the permitivity of free space, A is the circular area of bottom plate 608 and y is the distance between bottom plate 608 and top plate 602).

Figure 7:
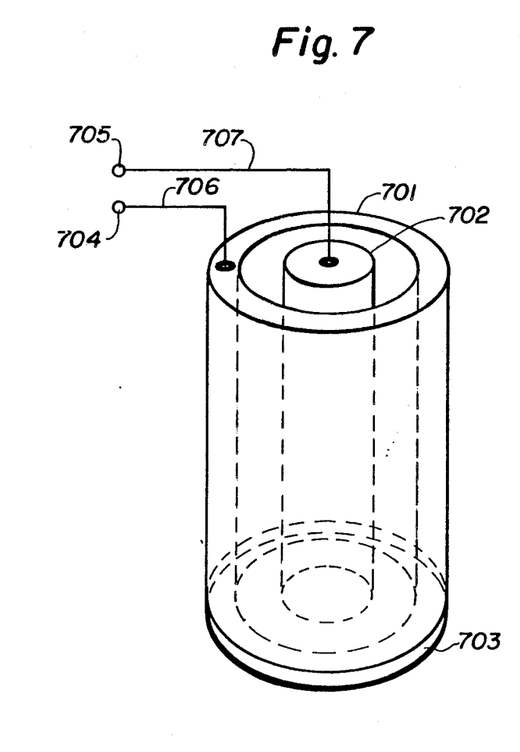
FIG. 7 shows a perspective view of a coaxial capacitive test cell in accordance with the instant invention.

FIG. 7 depicts an alternative version of a capacitive test cell also useful with the invention wherein conducting annulus 701 and conducting cylinder 702 are attached coaxially to non-conducting baseplate 703. Conducting wire 706 joins annulus 701 with connecting terminal 704. Conducting wire 707 joins cylinder 702 with connecting terminal 705. The capacitance of this cell is a function of the specific dimensions of its geometry as well as being directly related to the relative permitivity constant of the fluid suspension contained between cylinder 702 and annulus 701. Non-conducting base 703 may be perforated in the area between cylinder 702 and annulus 701 so as to allow the cell to be dipped into a fluid suspension in order to fill the cavity between cylinder 702 and annulus 701 with the fluid or to allow the fluid to flow therebetween.

Using the circuitry, apparatus, and source waveforms as described above, Applicants have done extensive experimental testing on various non-aqueous relatively low-permitivity fluid suspensions of charged particles. As a result of these experiments, Applicants have discovered several heretofore unknown graphical correlations which significantly improve the accuracy and efficiency of determining important properties of such suspensions. The following text, in accordance with FIGS. 9 through 15, provide specific examples of some of the ways the invention can be used to great advantage.

EXAMPLE 1

Measure of the adhesion of charged material to a substrate using low frequency voltammetry. See FIGS. 9 and 10.

Magenta electrostatic liquid developer (DX Imaging, Lionville, Pa.) having a mobility of $7.3\text{E-}10\ m^2/Vs$ was diluted to 1.5% solids in Isopar L ®. The cyclic voltammetry of the toner was measured in a 0.5 mm cell with electrode area of 10 cm$^2$. The voltage was scanned from $-1000$ volts to $+1000$ volts at a rate of 20 volts/second. The electrode materials were aluminum and indium tin oxide (ITO) coated glass. The adherance to the ITO coated glass was measured from cyclic voltammetry by plating the toner on the surface of interest and measuring the voltage required to remove the toner. This value was compared to the force required to remove the dried toner layer. The adhesion force was measured by attaching a 0.8 cm$^2$ block with Scotch double stick tape to the toner layer and pulling on the block to remove the toner from the substrate. The force to remove the toner layer from the ITO was measured with a balance attached to the block.

This experiment was then repeated with the exception that the ITO electrode was coated with a thin film of Elvacite ®. The cyclic voltammetry and force of adhesion of the toner layer to this substrate were measured.

In the cyclic voltammetry results, the scan corresponding to removal of magenta toner from the ITO or coated ITO electrode has two peaks in the current vs. voltage plot, one at about 200 volts and the other at about 300 volts. The relative ratio of these peaks changes with the use of different electrode materials indicating a differing adhesive force.

| Electrode | voltammetry peak ratio (200v/300v) | Adhesive Force |
| --- | --- | --- |
| ITO | 0.68 | 3.6 lbs |
| Elvacite ® | 1.08 | 3.2 lbs |

EXAMPLE 2

Use of voltammetry as fingerprint technique for identifying electrical properties of suspension that can reflect performance differences. See FIGS. 11 and 12.

Cyan toner produced by DX Imaging, Lionville, Pa. was diluted to 1.5% solids. The toner mobility was $6\text{E-}10\ m^2/Vs$. The toner performance was evaluated by imaging electrostatically onto a photopolymer film and electrostatically transferring the toned image from the photopolymer to paper. The photopolymer was exposed imagewise through a halftone film. The fixture used for toner evaluation consists of a 36 inch circumference drum, on which the imaged photopolymer is mounted. The drum is rotated at 2.2 inches/second, causing the photopolymer film to pass through various process stations. First, the film is charged with a scorotron, the grid being operated at $+200$ volts and the wire at 5.0 kV. After charging (2 sec) the film is passed through a toning station consisting of two rollers spaced 0.006 inches from the master, the gaps being filled with a flow of liquid electrostatic toner. Excess toning fluid is then removed from the film with a rotating metering roller spaced 0.004 inches from the master. The metering roller is biased to 120 volts to remove toner from the background areas. Transfer to paper is accomplished with the combination of a conductive rubber roller, operated at $-3.5$ kV, and a transfer corotron, operated at $+4.0$ to 5.5 kV. Paper is placed between the toned image and the conductive rubber roller, which lays against the drum and thus brings the paper in contact with the toned image. The paper is then passed under the corotron, affording transfer of the toned image to the paper. The image is fixed to the paper by fusing (110 C for 45 sec).

The image on paper gave a dot range of 3–98.5% dots and the image had good solid area uniformity and no smear.

The cyclic voltammetry of the toner was measured in a 1.0 mm cell with electrode area of 10 cm$^2$. The voltage was scanned from $-1000$ volts to $+1000$ volts at a rate of 20 volts/second. The electrode materials were aluminum and indium tin oxide (ITO) coated glass. The cyclic voltammetry measures 0.1 pmhos/cm steady state conductivity and a peak in the capacitive current at 250 volts.

The procedure outlined above was followed except 70 mg of Triton X35 (Rohm and Haas) was added per gram of toner solids. The mobility of the toner was 7.7E-10 m²Vs. In the image, the dot range was reduced to 4–95% dots and the image showed increased solid area non-uniformity and smear. The cyclic voltammetry gives 2.68 pmhos/cm steady state conductivity and a shift in the capacitive peak current to 100 volts. The increased DC conductivity and decreased toner adhesion are differences detected in the cyclic voltammetry which reflect differences in toner performance.

EXAMPLE 3

Use of low frequency voltammetry as a technique for quality control in that toners with similar voltammetric fingerprints have similar performance characteristics. See FIG. 13.

Figure 13:
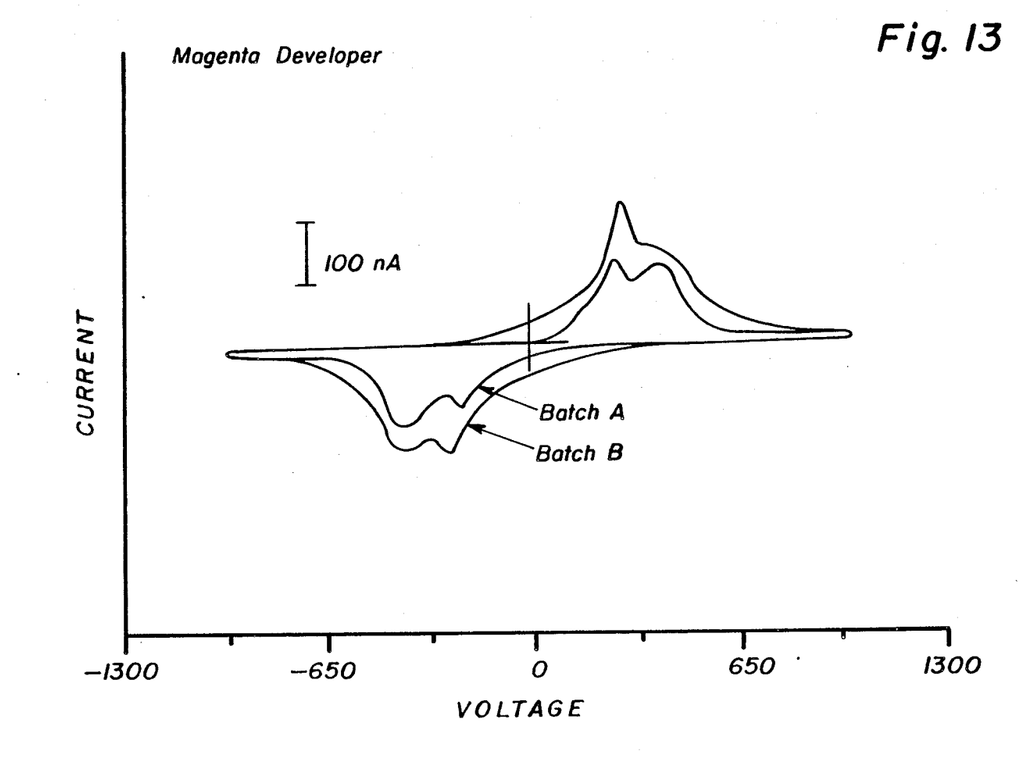
FIG. 13 depicts results from low frequency voltammetry of magenta developer manufactured in separate batches. Conditions are as described above for the system of FIG. 9.
Figure 14:
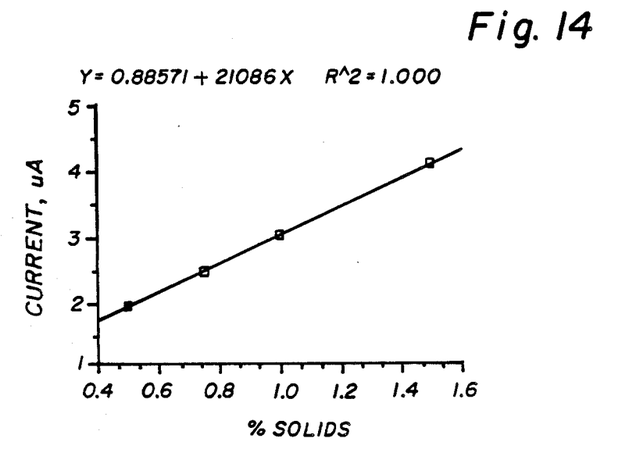
FIG. 14 shows high-frequency voltammetry results for measuring the weight percent of solids in a developer suspension at fixed mobility.
Figure 15:
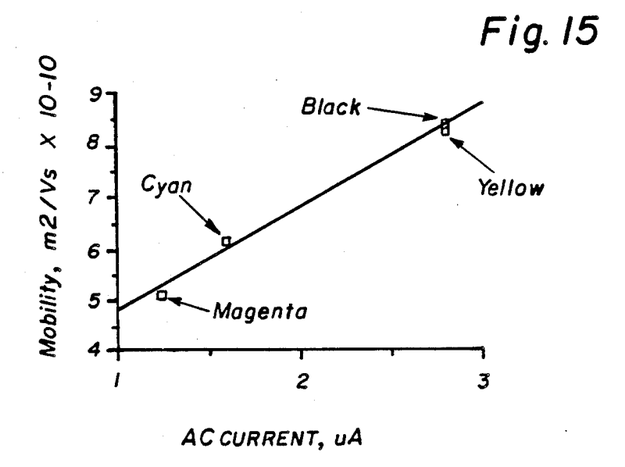
FIG. 15 shows high-frequency voltammetry results for determining the mobility of a developer suspension at fixed concentration.

Cyclic voltammetry of two different batches of magnets liquid developer (DX Imaging) manufactured by the same method and containing the same material composition are shown in FIG. 13. The voltammetry was measured in the same way as in Example 1. Mobilities of the two batches were measured to be $5.57 \times 10^{-10}$ $m^2/Vs$ and $8.66 \times 10^{-10}$ $m^2/Vs$ for batch a and b respectively. The difference in mobility shows up as a difference in the integrated peak area in FIGS. 5A and 5B. Peak shapes and peak voltages, however, are closely matched. Images were made with these toners on a Savin 8700 copier and evaluated as follows:

| Toner | Paper | Density | Transfer efficiency | Resolution line pairs/mm |
|---|---|---|---|---|
| Magenta toner Batch A | smooth | 2.07 | 77% | 2.8 |
| | rough | 1.42 | 74% | 4.0 |
| Magenta toner Batch B | smooth | 2.16 | 79% | 3.0 |
| | rough | 1.45 | 71% | 4.0 |

The toners behaved very similarly with regard to resolution, density and transfer efficiency.

EXAMPLE 4

Use of high frequency voltammetry as a method for measuring the weight percent of solids in developer suspensions at fixed mobility. See FIG. 14.

Cyan electrostatic liquid developer (DX Imaging, Lionville, Pa.) having a mobility of $6.14 \times 10^{-10} m^2/Vs$ was diluted from working strength, 1.5% solids developer to a variety of concentrations with supernatant obtained by centrifugation of the developer. The developer was placed between aluminum electrodes of area 10 cm² separated by 0.5 mm. The voltage varied linearly between +500 and −500 V at a frequency of 40 Hz. The amplitude of the current signal due to the toner was measured on an oscilloscope.

The amplitude of the current response increases with increasing concentration of developer solids in a linear fashion. Results are shown in the following table and the graph of FIG. 14.

| % solids | amplitude, uA |
|---|---|
| 0.50 | 1.95 |
| 0.75 | 2.45 |
| 1.00 | 3.00 |
| 1.50 | 4.05 |

EXAMPLE 5

Use of high frequency voltammetry to determining the mobility of developer suspensions at fixed concentration. See FIG. 15.

Four colored developers, yellow, black, cyan and magents (DX Imaging, Lionville, Pa.) were diluted 1.5% solids with Isopar L ® and tested by high frequency voltammetry for AC current amplitude and by ESA (Matek Inc., Hopkinton, Mass.) for mobility. High frequency voltammetry was carried out as in Example 1. AC current in linearly proportional to mobility for these developers. Results are given in the following table and the graph of FIG. 15.

| Toner | AC current, uA | Mobility, $m/Vs \times 10^{-10}$ |
|---|---|---|
| Yellow | 2.80 | 8.22 |
| Black | 2.80 | 8.33 |
| Cyan | 1.60 | 6.14 |
| Magenta | 1.25 | 5.12 |

What is claimed is:

1. A method for determining the mobility of charged particles of a non-aqueous liquid test suspension of said charged particles, said suspension having a relative dielectric constant of less than 15, said method comprising the steps of:
   (a) placing said suspension between two electrodes, said electrodes comprising capacitive elements;
   (b) subjecting said suspension to a regularly varying electric field via said electrodes, wherein said electric field varies at a frequency greater than one Hertz and has a peak magnitude greater than one thousand volts per centimeter;
   (c) measuring the resulting electric current through said suspension; and
   (d) comparing said electric current to predetermined currents representative of the mobility of substantially similar suspensions.

2. A method for determining the concentration of charged particles of a non-aqueous liquid test suspension of said charged particles, said suspension having a relative dielectric constant of less than 15, said method comprising the steps of:
   (a) placing said suspension between two electrodes, said electrodes comprising capacitive elements;
   (b) subjecting said suspension to a regularly varying electric field via said electrodes, wherein said electric field varies at a frequency greater than one Hertz and has a peak magnitude greater than one thousand volts per centimeter;
   (c) measuring the resulting current through said suspensions; and
   (d) comparing said electric current to predetermined currents representative of the concentration of substantially similar suspensions.

3. A method in accordance with claim 1 wherein said electric field is a symmetrical alternating field.

4. A method in accordance with claim 3 wherein said alternating field is sinusoidal.

5. A method for determining the adhesive strength of charged particles of a non-aqueous liquid test suspension of said charged particles, said suspension having a relative dielectric constant of less than 15, said method comprising the steps of:

(a) placing said suspension between two electrodes, said electrodes comprising capacitive elements;

(b) subjecting said suspension to a regularly varying electric field via said electrodes, wherein the voltage creating said electric field is substantially an alternating linear ramp having a time rate of change greater than 10 volts per second and a frequency of less than 0.1 Hertz;

(c) observing the resulting electric current waveforms passing through said suspensions; and (d) comparing said electric current waveforms to predetermined current waveforms representative of the adhesive strength of the charged particles in substantially similar suspensions.

6. A method in accordance with claim 5 wherein said suspension comprises a cosmetic.

7. A method in accordance with claim 5 wherein said suspension comprises a paint.

8. A method in accordance with claim 5 wherein said suspension comprises a ceramic.

9. A method in accordance with claim 1 wherein said suspension comprises a cosmetic.

10. A method in accordance with claim 1 wherein said suspension comprises a paint.

11. A method in accordance with claim 1 wherein said suspension comprises a ceramic.

12. A method in accordance with claim 1 wherein said suspension comprises an electrostatic toner.

13. A method in accordance with claim 5 wherein said suspension comprises an electrostatic toner.

14. A method according to claim 2 including an additional step of using the concentration of the charged particles of the test suspension thus determined as a control factor for an automatic system designed to hold the concentration of the charged particles of said test suspension within a desired range.

15. A method according to claim 1 including an additional step of using the mobility of the charged particles of the test suspension thus determined as a control factor for an automatic system designed to hold the mobility of the charged particles of said test suspension within a desired range.

16. A method in accordance with claim 2 wherein said suspension comprises an electrostatic toner.

17. A method in accordance with claim 2 wherein said electric field is a symmetrical alternating field.

18. A method in accordance with claim 17 wherein said alternating field is sinusoidal.

19. A method in accordance with claim 2 wherein said suspension comprises a cosmetic.

20. A method in accordance with claim 2 wherein said, suspension comprises a paint.

21. A method in accordance with claim 2 wherein said suspension comprises a ceramic.

* * * * *